United States Patent [19]

Ono

[11] Patent Number: 4,596,779
[45] Date of Patent: Jun. 24, 1986

[54] CULTURE VESSEL WITH AGITATOR
[75] Inventor: K. R. Ono, Bridgeton, N.J.
[73] Assignee: Bellco Glass, Inc., Vineland, N.J.
[21] Appl. No.: 488,916
[22] Filed: Mar. 23, 1983
[51] Int. Cl.$^4$ .................. C12M 3/02; C12M 1/12; C12M 1/02; C12M 3/00
[52] U.S. Cl. .................. 435/286; 435/311; 435/316; 435/284; 435/285; 366/195
[58] Field of Search ............. 435/284, 286, 285, 311, 435/316, 813; 366/191, 194, 195, 196

[56] References Cited
U.S. PATENT DOCUMENTS

| 426,954 | 4/1890 | Parsons | 239/142 |
|---|---|---|---|
| 2,595,793 | 5/1952 | Kay | 435/284 X |
| 3,468,520 | 9/1969 | Duryea et al. | 259/39 |
| 3,647,632 | 3/1972 | Johnson et al. | 435/311 |
| 3,831,850 | 8/1974 | Hunter | 239/144 |
| 3,847,750 | 11/1974 | Ridgeway, Jr. et al. | 435/316 X |
| 4,166,768 | 9/1979 | Tolbert et al. | 435/286 |
| 4,178,209 | 12/1979 | Tolbert et al. | 435/286 X |
| 4,204,774 | 5/1980 | deBruyne | 366/102 |
| 4,355,906 | 10/1982 | Ono | 366/274 |
| 4,382,685 | 5/1983 | Pearson | 435/316 X |
| 4,535,062 | 8/1985 | Muller | 435/316 X |

FOREIGN PATENT DOCUMENTS 0073079 3/1983 European Pat. Off. ............ 435/311

Primary Examiner—Robert J. Warden
Assistant Examiner—Randall E. Deck
Attorney, Agent, or Firm—Seidel, Gonda, Goldhammer & Abbott

[57] ABSTRACT

A culture vessel has an agitator arranged to orbit about an upright axis while being hollow at least at one end. A filter is provided on said one end and a conduit communicates with the hollow portion of the agitator for withdrawing filtered fluid from the vessel as the agitator orbits.

14 Claims, 5 Drawing Figures

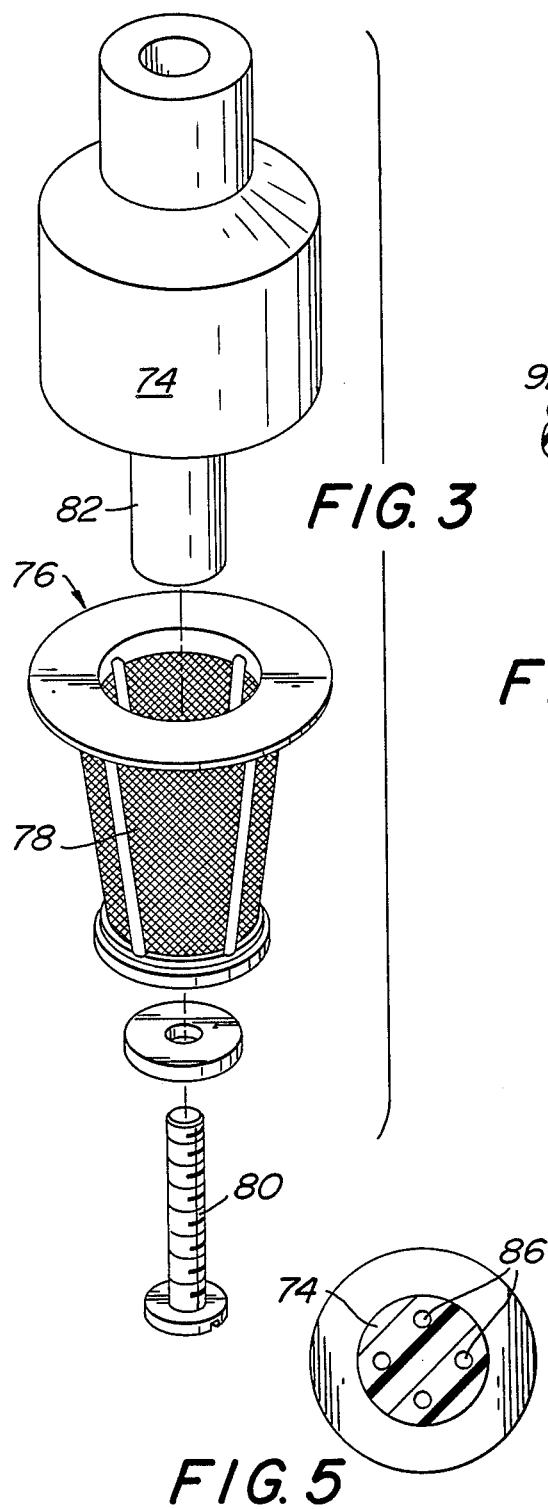
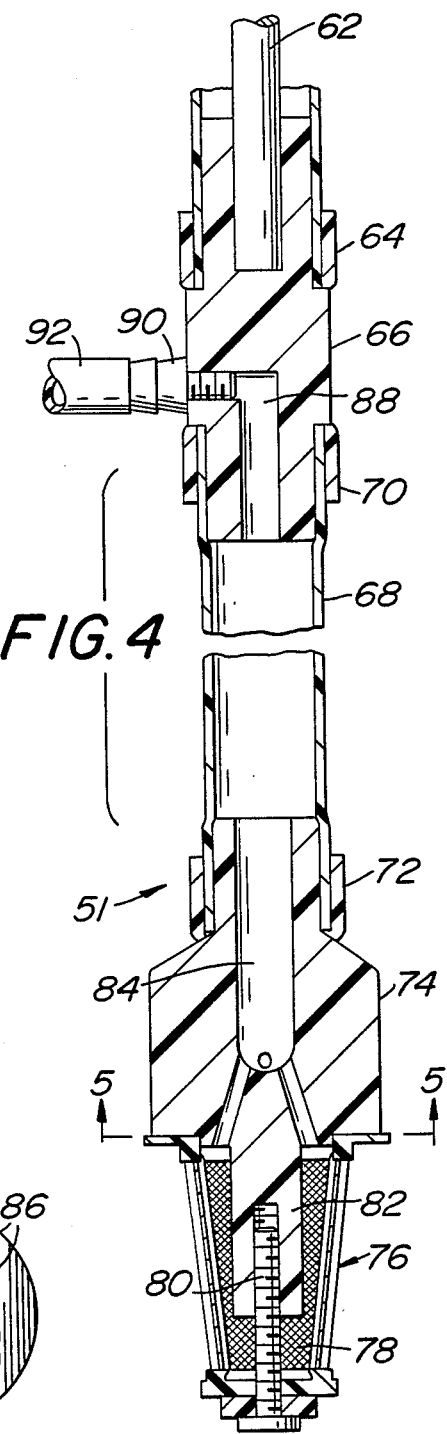

CULTURE VESSEL WITH AGITATOR

BACKGROUND

A culture vessel with an agitator is disclosed in U.S. Pat. No. 4,355,906. As noted in said patent, it is necessary to agitate a culture media containing microcarrier beads in order to maintain the beads in suspension. It is desireable to have a continuous perfusion culture system which involves removing media from the culture vessel and adjusting a parameter of the media such as its Ph or oxygen content. It may be more desireable to adjust the media in a vessel which is separate from the culture vessel. A medium recycling system and a continuous perfusion culture system requires a filter to prevent the culture from leaving the culture vessel. When a filter has been utilized heretofore for that purpose, the beads and/or cultures clog up the filter as the media is being drawn out of the vessel. As a result thereof, it was necessary to stop the agitation and allow the beads to settle out. It may under certain conditions be undesireable to stop agitation of the culture media.

The present invention is directed to a solution of overcoming the above problem whereby agitation of the culture medium need not be stopped due to filter clogging and addresses itself to solving the problem of providing a vessel which can be used in a true continuous perfusion culture system.

SUMMARY OF THE INVENTION

The present invention is directed to a culture vessel having an agitator arranged to orbit about an upright axis within the vessel. The agitator is hollow at least at one end. A filter is provided on said one end in a manner so that the filter will be subjected to a shearing action as the agitator orbits. A conduit means communicates with the hollow portion of he agitator for facilitating the change of media and other material from the vessel as the agitator orbits. The vessel has an inlet for introducing a fluid into the vessel while the agitator orbits.

The primary object of the present invention is to provide a culture vessel which permits continuous withdrawal and return of media and other material without stopping agitation and without filter clogging problems.

Various objects and advantages of the present invention will appear hereinafter.

For the purpose of illustrating the invention, there is shown in the drawings a form which is presently preferred; it being understood, however, that this invention is not limited to the precise arrangements and instrumentalities shown.

FIG. 3 is an exploded view of the filter and its support.

FIG. 4 is a longitudinal sectional view of a portion of the agitator as indicated by the elipse in FIG. 2.

FIG. 5 is a sectional view taken along the line 5—5 in FIG. 4.

DETAILED DESCRIPTION

Figure 1:
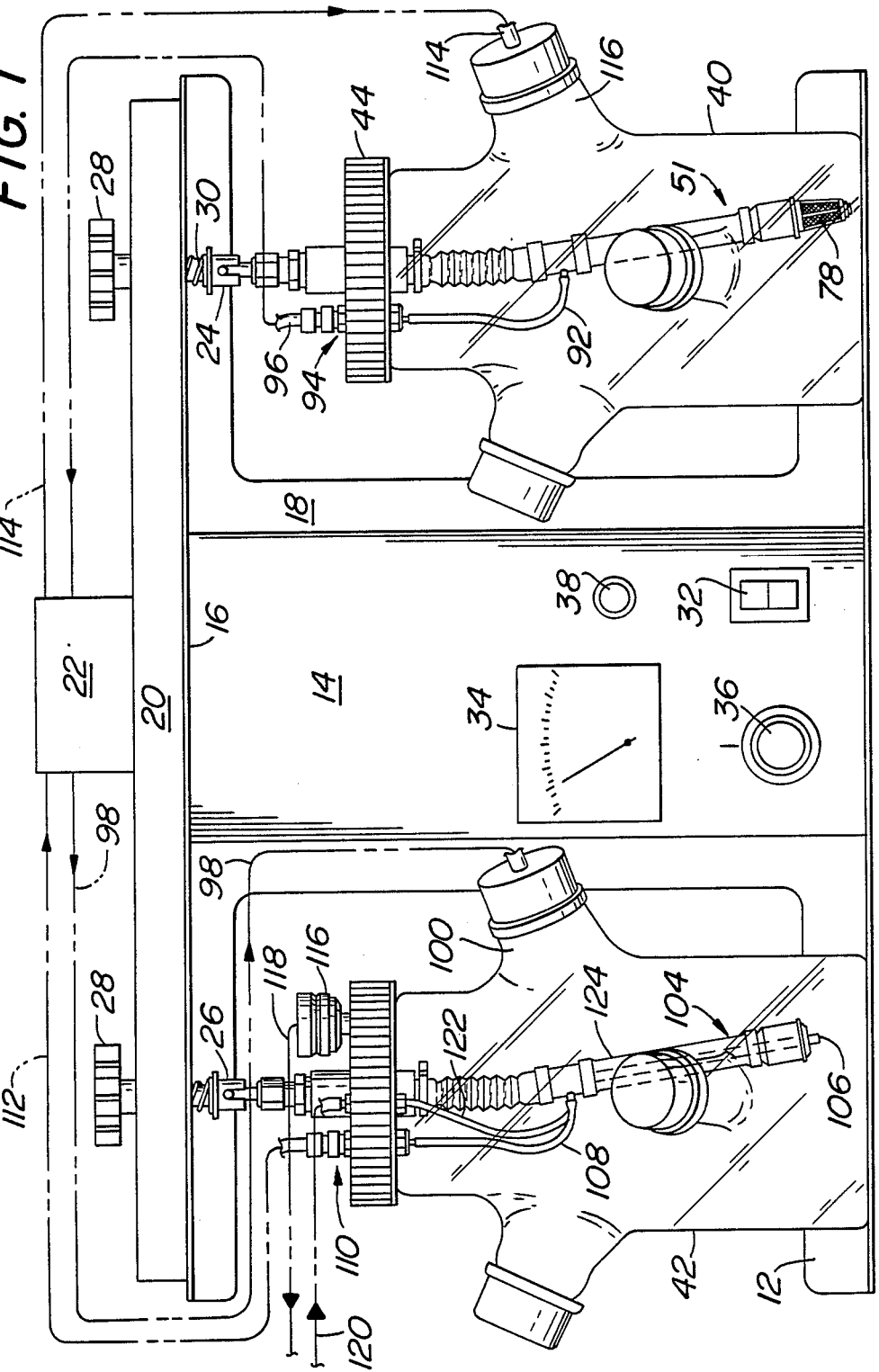
FIG. 1 is a elevation view of a continuous profusion culture system.

Referring to the drawings in detail, wherein like numerals indicate like elements, there is shown in FIG. 1 a continuous perfusion culture system. The system may include a support base 12 on which is provided a drive unit housing 14. A horizontal platform 16 is connected to the base 12 by a vertical wall 18 and overlies the top wall of the housing 14. On the platform 16, there is provided a housing 20 containing a chain and sprocket or equivalent preferably driven by a motor not shown within the housing 14. On the housing 20, there is provided a pump 22.

The chain and sprockets in housing 20 are connected to vertically disposed output shafts 24 and 26. The speeds of pump 22 and shafts 24; 26 are correlated to increase and decrease proportionally. Each shaft is biased downwardly by a coil spring 30 and may be raised vertically by a handknob 28. The housing 14 includes an on/off switch 32, meter 34 for indicating motor speed, a motor speed adjusting knob 36, and a fuse 38.

On the right hand side of FIG. 1 there is illustrated a culture vessel 40 which is releasably coupled to the drive shaft 24 while being supported by the base 12. As shown at the left hand end of FIG. 1, a media vessel 42 is releasably coupled to the drive shaft 26 while being supported by the base 12.

Figure 2:
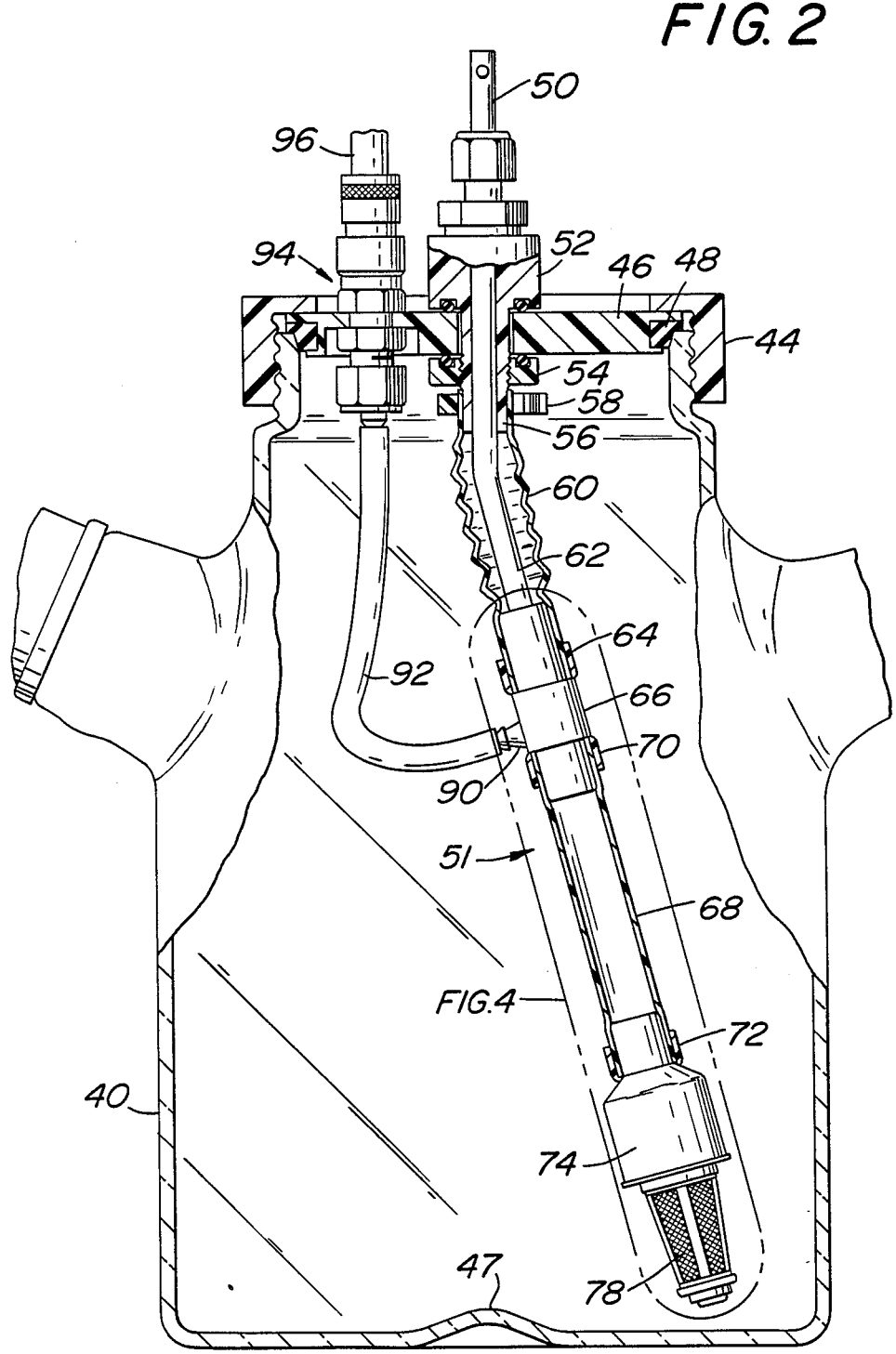
FIG. 2 is a vertical sectional view of the culture vessel.

As shown more clearly in FIG. 2, the vessel 40 is a sealed vessel having a cap 44 threaded to the upper end of vessel 40. Cap 44 overlies an insert 46 having a seal 48 on its circumference and in contact with the vessel opening at the corner thereof. A central portion 47 of the vessel bottom wall is convex on the inner surface. A drive shaft 50 is provided for causing an agitator 51 to orbit within the vessel 40. At it upper end the drive shaft 50 is straight and disposed along the longitudinal axis of the vessel 40. A radially disposed pin at the upper end of the drive shaft 50 is adapted to be connected to the drive shaft 24 after the latter has been raised by knob 28 and then released.

The straight portion of the drive shaft 50 extends through a bearing 52 which is sealed to and mechanically connected to the insert 46 by nut 54. The bearing 52 has an axial extension 56.

One end of a transparent corrugated plastic sleeve 60 is telescoped over the extension 56 and held by clamp 58. The sleeve 60 surrounds the bent or angled portion 62 of the drive shaft 50. The longitudinal axis of portion 62 is at an acute angle with respect to the longitudinal axis of he straight portion of the drive shaft 50. The free end portion 62 is rotatably connected to a distributor head 66.

The lower end of the sleeve 60 is attached to a reduced diameter portion on the upper end of distributor head 66 by a collar 64. Referring to FIGS. 2 and 4, a reduced diameter portion on the lower end of the distributor head 66 is connected to the upper end of a rigid plastic tube 68 by a collar 70. The lower end of tube 68 is connected to the upper end of a filter head 74 by a collar 72. Tube 68, sleeve 60 and head 74 may be made from an inert polymeric plastic material or any other suitable material.

The head 74 supports a filter housing 76 as shown more clearly in FIGS. 3 and 4. Housing 76 is removably attached to the head 74 in any convenient manner and supports filter 78 which forms an extension of the filter head 74 and preferably is annular in shape. The housing 76 is preferably connected to the filter head by way of a bolt 80 threaded to the extension 82.

The filter head 74 has a flow passage 84 communicating at its upper end with the tube 68. Passage 84 communicates at its lower end with the interior of the filter 78 by way of a plurality of flow passages 86. See FIGS. 4 and 5. The upper end of the tube 68 communicates with a right angle flow pasage 88 in the distributor head 66.

A tube connector 90 has one end connected to the distributor head 66 and its other end connected to one end of a flexible withdrawal tube 92. Tube 92 communicates with the interior of the vessel 40 by way of connector 90, passage 88, tube 68, passages 84 and 86, and filter 78.

The upper end of tube 92 is connected to one end of a conduit 96 by way of a connector 94 supported by the insert 46. Due to the fact that the agitator 51 orbits but does not rotate, tube 92 does not wrap around the agitator 51 during operation.

Referring to FIG. 1, the other end of conduit 96 is connected to a first suction port in the pump 22. The outlet port opposite the first suction port in the pump 22 is connected to one end of conduit 98. The outer end of conduit 98 is connected to a flow passage in a removable cap attached to the sample port 100 on vessel 42. Thus, any media or other material removed from vessel 40 will be transmitted to the vessel 42 while the agitator 51 orbits in vessel 40.

Within the vessel 42, there is provided an agitator 104 which is the same as agitator 51 except as will be made clear hereinafter. Agitator 104 does not have a filter comparable to filter 78. Agitator 104 has concentric tubes with the inner tube designated 106. Tube 106 is in direct communication with any media in vessel 42 at its lower end. The upper end of tube 106 is connected by way of a distributor head to one end of flexible tube 108. The other end of flexible tube 108 is connected one end of conduit 112 by way of a connector 110 on the cap insert. The other end of conduit 112 is connected to a second suction port on the pump 22. The second outlet port in pump 22 communicates with one end of conduit 114. The other end of conduit 114 is connected to the interior of vessel 40 by way of a removable cap attached to the sample port 116. Thus, while the agitators 51 and 104 orbit, media or other material may continuously flow from vessel 40 to vessel 42 and then return to vessel 40 without any clogging problems. In order to render such flow intermittant, it is only necessary to shut off pump 22 which may be timer controlled.

Referring to the left hand end of FIG. 1, the tube 106 is surrounded by a transparent tube 124. The space between the tubes 106 and 124 at its lower end communicates with the interior of vessel 42 and at its upper end communicates with one end of the flexible tube 122. The other end of tube 122 is connected to a conduit 120 by way of a connector supported by the cap insert. Conduit 122 facilitates introducing fluids into the vessel 42 such as liquids intended to adjust the Ph of the media. If desired, a connector 116 may communicate at one end with the interior of the vessel above the level of media and connnected to a suction withdrawal conduit 118 for removal of gases above media level within the vessel 42.

The filter 78 performs multiple functions. Thus, filter 78 performs an agitating function since it is part of the agitator 51. Filter 78 facilitates continuous or intermittant exchange of media between vessels 40, 42 without stopping the movement of the agitator. The filter 78 may be used to facilitate extraction of any viral byproduct from the vessel 40. The filter 78 may act as a cell sieve for collection of cells which have separated from the beads. With beads in the range of 80 to 100 microns, it is preferable to use a 50 micron filter for the filter 78.

The present invention facilitates using large vessels with separate motors connected to the agitators. The vessels 40, 42 may be rapidly connected and disconnected to their respective drive shafts 24, 26. All portions of the agitators are made from inert plastic materials except shaft 50 so that there is no direct contact between the media and any portion of the agitator which may introduce undesirable material into the media. The vessels are sealed vessels. In view of the above, it will be seen that the present invention does facilitate non-stop recycling and/or a true continuous profusion culture system while including a culture vessel which solves a variety of problems.

The present invention may be embodied in other specific forms without departing from the spirit essential attributes thereof and, accordingly, reference should be mde to the appended claims, rather than to the foregoing specification, as indicating the scope of the invention.

I claim:

1. Apparatus comprising a culture vessel having an agitator arranged to orbit about a generally upright longitudinal axis of the vessel, said agitator being hollow at least at a free end thereof, a filter supported on and constituting an extension of said free end, and conduit means communicating with the hollow portion of the agitator for withdrawing a substance from the vessel via said agitator orbits, said vessel having an inlet for introducing a substance into the vessel while said agitator orbits, and wherein said agitator orbits but does not rotate.

2. Apparatus in accordance with claim 1 including a rod having one portion lying along the longitudinal axis of the vessel and configured so as to be connected to a motor, another portion of said rod being at an acute angle with respect to said longitudinal axis, and a sleeve surrounding said angled portion of said rod, and wherein said angled end portion of said rod supports said agitator.

3. Apparatus in accordance with claim 1 wherein said filter is annular and has one end attached to said free end.

4. Apparatus in accordance with claim 1 wherein the upper end of said vessel is sealed by a removable cap, said agitator having a drive portion extending through a portion of said cap, said conduit means including a flexible conduit having one end attached to a connector on a portion of said cap.

5. Apparatus in accordance with claim 1 wherein said filter is generally, a truncated cone.

6. Apparatus in accordance with claim 5 wherein said conduit means communicates the hollow portion of said agitator by a passage generally perpendicular to the conical axis of said filter.

7. Apparatus in accordance with claim 1 wherein said agitator includes bearing means supporting said agitator on said vessel; a drive shaft having a straight upper end portion disposed along said upright longitudinal axis and a lower angle portion at an acute angle with respect to said upright longitudinal axis, said straight end portion extending through said bearing means; a distribution portion supporting the hollow portion of the agitator and having a bore in which an end portion of said angled portion of said drive shaft is rotatably disposed; and a flexible sleeve surrounding at least a portion of said straight end portion and said angle portion, said flexible sleeve being attached to said distribution portion whereby said end portion of said angle portion rotates within said distribution portion bore.

8. Apparatus comprising a culture vessel sealed by a cover means thereon, an agitator extending through said cover means and having a free end adjacent to the bottom of said vessel for orbital movement about a generally upright axis of said vessel, a flexible conduit having one end coupled to a connector at said cover means, the other end of said conduit communicating with one end of a flow passage movable with said agitator free end, the other end of said flow passage communicating with the interior of said vessel by way of a filter means having a filtering surface, said filter means being movable with said agitator and arranged to facilitate filtering of substances withdrawn via said passage and said flexible conduit, and wherein said agitator orbits but does not rotate, and said flexible conduit does not wrap around the agitator during operation as said agitator and filter means orbits in a media within said vessel.

9. Apparatus in accordance with claim 8 including a second vessel communicating with said flexible conduit by way of a pump, an agitator in said second vessel, conduit means communicating said second vessel with said first mentioned vessel by way of said pump, motor means connected to each agitator, and means for introducing substances into said second vessel.

10. Apparatus in accordance with claim 8 wherein said filter means includes an annular filter removably attached to said free end of said agitator, said flow passage being within said agitator.

11. Apparatus in accordance with claim 10 wherein said agitator includes a drive shaft having a straight portion along the axis of said vessel and an angled portion at an acute angle with respect to said axis, said angled portion being surrounded by a flexible sleeve, said filter means being attached to said flexible sleeve.

12. Apparatus in accordance with claim 8 wherein said flow passage is perpendicular to a longitudinal axis of said agitator at the end communicating with said flexible conduit.

13. Apparatus comprising a culture vessel having an agitator, said agitator being hollow at least at a free end thereof; a filter supported on and constituting an extension of said free end, said filter having a longtudinal axis and being arranged to orbit about a generally upright axis of the vessel; and conduit means communicating with the hollow portion of said agitator for withdrawing a substance from the vessel via said agitator as the agitator orbits, said vessel having an inlet for introducing a substance into the vessel while said agitator orbits, said agitator including bearing means and a distribution portion, said bearing means supporting said agitator on said vessel, and wherein said agitator orbits but does not rotate.

14. Apparatus in accordance with claim 13 wherein said agitator includes a drive shaft having a straight upper end portion disposed along said upright axis and a lower angled portion at an acute angle with respect to said upright axis, and a flexible sleeve surrounding at least a portion of said straight end portion and said angled portion, said distribution portion having a bore in which the end of said angled portion of said drive shaft opposite said upper end portion of said drive shaft is rotatably disposed, said flexible sleeve being attached to said distribution portion such that said lower angled portion of said drive shaft rotates within the bore of said distribution portion.

* * * * *